US009125900B2

(12) United States Patent
Meyer

(10) Patent No.: US 9,125,900 B2
(45) Date of Patent: Sep. 8, 2015

(54) PHARMACEUTICAL COMPOSITION

(75) Inventor: Leith Carl Rodney Meyer, Edenglen (ZA)

(73) Assignee: University of the Witwatersrand, Johannesburg, Johannesburg (ZA)

( * ) Notice: Subject to any disclaimer, the term of this patent is extended or adjusted under 35 U.S.C. 154(b) by 47 days.

(21) Appl. No.: 12/066,525

(22) PCT Filed: Sep. 14, 2006

(86) PCT No.: PCT/IB2006/002521
§ 371 (c)(1),
(2), (4) Date: Jul. 25, 2008

(87) PCT Pub. No.: WO2007/031846
PCT Pub. Date: Mar. 22, 2007

(65) Prior Publication Data
US 2009/0203733 A1      Aug. 13, 2009

(30) Foreign Application Priority Data

Sep. 14, 2005   (ZA) ................................. 2005/07377
Nov. 9, 2005    (ZA) ................................. 2005/09323

(51) Int. Cl.
| A61K 31/439 | (2006.01) |
| A61P 11/00  | (2006.01) |
| A61K 31/405 | (2006.01) |
| A61K 45/06  | (2006.01) |

(52) U.S. Cl.
CPC .............. *A61K 31/405* (2013.01); *A61K 45/06* (2013.01)

(58) Field of Classification Search
USPC ........................................................ 514/304
See application file for complete search history.

(56) References Cited

U.S. PATENT DOCUMENTS

| 5,057,519 A        | 10/1991 | Suberg        |
| 2002/0091235 A1    | 7/2002  | Sibley et al. |
| 2003/0130355 A1 *  | 7/2003  | Heal et al. ........................ 514/650 |
| 2003/0139422 A1 *  | 7/2003  | Teng ........................ 514/252.15 |
| 2005/0203103 A1    | 9/2005  | Jasti et al.   |

FOREIGN PATENT DOCUMENTS

| DE | 19953625 A1    |   | 5/2001 |
| WO | WO 02/88139    | * | 4/2001 |
| WO | WO2005004865 A1 |  | 1/2005 |
| WO | WO2005063712 A1 |  | 7/2005 |

OTHER PUBLICATIONS

Ogawa (Comparison of 5-Hydroxytryptamine-Induced Contraction of Rat Pulmonary Artery to That of Aorta in Vitro, Japanese Circulation Journal, vol. 59, Feb. 1995).*
Marcos (Serotonin Trnsporter Inhibitors Protect against Hypoxid Pulmonary Hypertension, Am. Journal Respir Crit Care Med, vol. 168, (2003) pp. 487-493).*
Sahibzada (Reversal of Morphine-induced Apnea in the Anesthetized Rat by Drugs that Activate 5-Hydroxytryptamine1A Receptors, Journal of Pharmacology and Experimental Therapeutics, 2000, vol. 292, No. 2, pp. 704-713).*
Lamarche (The sleep apnoea syndrome and epidural morphine, Cancer Anaesth Soc, 1986, 33;2 pp. 231-233).*
Supplemental European Search Report completed May 16, 2013, which issued in corresponding EP Application No. EP06795481.

* cited by examiner

*Primary Examiner* — Kathrien Cruz
(74) *Attorney, Agent, or Firm* — Fish & Richardson P.C.

(57) ABSTRACT

This invention relates to a pharmaceutical composition for mammals and, more particularly, to a pharmaceutical composition which enhances the action of an anaesthetic used in both human and veterinary applications, which, at least partly, reduces the risk of respiratory depression and enhances pulmonary perfusion. The pharmaceutical composition is characterized in that it contains a serotonergic ligand or any pharmacologically acceptable salt or ester thereof which acts on at least one member of the 5-HT family of serotonergic receptors, preferably on one or more of the 5-HTiA, 5-HT4 and 5-HT7 serotonergic receptors. In an example the ligand is the 8-OH-DPAT ligand. The composition can be used in conjunction with or include an anaesthetic, preferably an opioid anaesthetic, to induce a state of anaesthesia in mammals and it can be used to immobilize wile or non-domestic mammals.

8 Claims, 7 Drawing Sheets

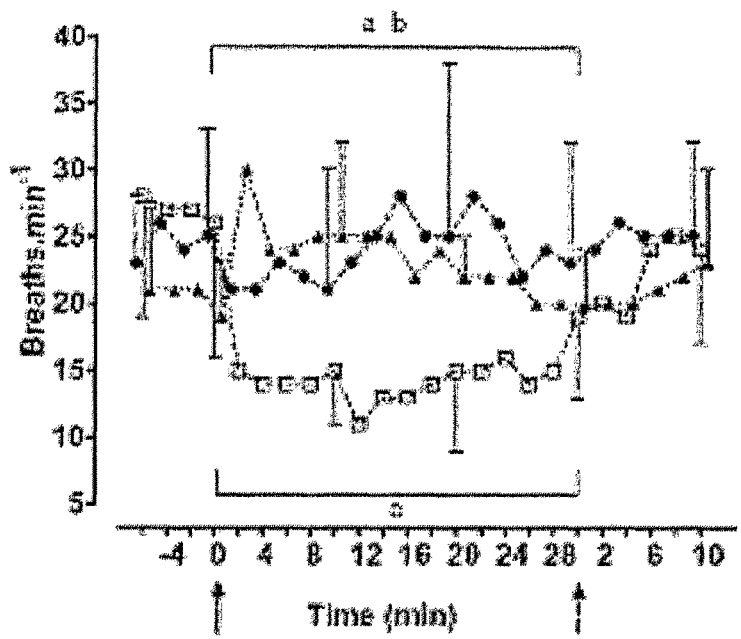

Fig. 1. Drug effects on respiratory rate over time. Values are respiratory rate (means, SD, $n = 8$) of goats injected (solid arrow, time = 0 min) with (intramuscular + intravenous) etorphine + water (□), etorphine + zacopride (●), and etorphine + 8-hydroxy-2-(di-n-propylamino)tetralin (8-OH-DPAT) (▲). Dashed arrow (time = 30 min) indicates intravenous injection of diprenorphine. $^{a}P$ <0.05, etorphine + zacopride vs. etorphine + water; and $^{b}P$ <0.05, etorphine + 8-OH-DPAT vs. etorphine + water [1-way ANOVA with post hoc Student-Newman-Keuls (SNK) test on areas between the curves]. $^{c}P$ <0.025, etorphine + water preinjection vs. postinjection (Student's paired $t$-test). Respiratory rates were not significantly different among the trials before the agents were injected ($F = 3.1, P = 0.19$).

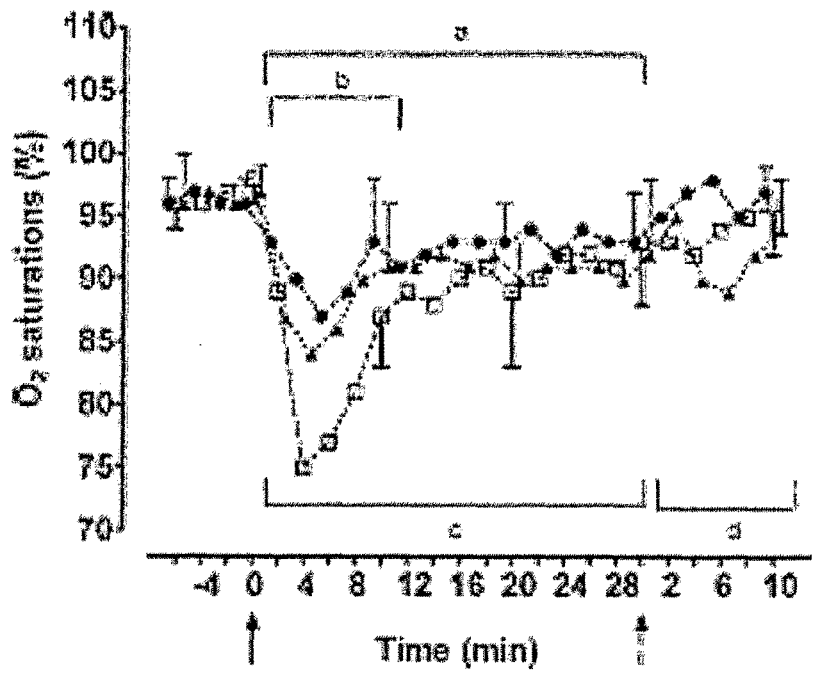

Fig. 2. Drug effects on percent hemoglobin saturation of arterial blood by oxygen. Values are percent saturation (means, SD, $n$ = 8) of goats injected (solid arrow, time = 0 min) with (intramuscular + intravenous) etorphine + water (□), etorphine + zacopride (●), and etorphine + 8-OH-DPAT (▲). Dashed arrow (time = 30 min) indicates intravenous injection of diprenorphine. $^aP$ <0.0125, etorphine + zacopride vs. etorphine + water; and $^bP$ <0.0125, etorphine + 8-OH-DPAT vs. etorphine + water (1-way ANOVA with post hoc SNK test on areas between the curves). $^cP$ <0.025, etorphine + water preinjection vs. postinjection; and $^dP$ <0.025, etorphine + 8-OH-DPAT preinjection vs. postreversal (Student's paired $t$-test). Saturation values were not significantly different among the trials before the agents were injected ($F$ = 0.1, $P$ = 0.9).

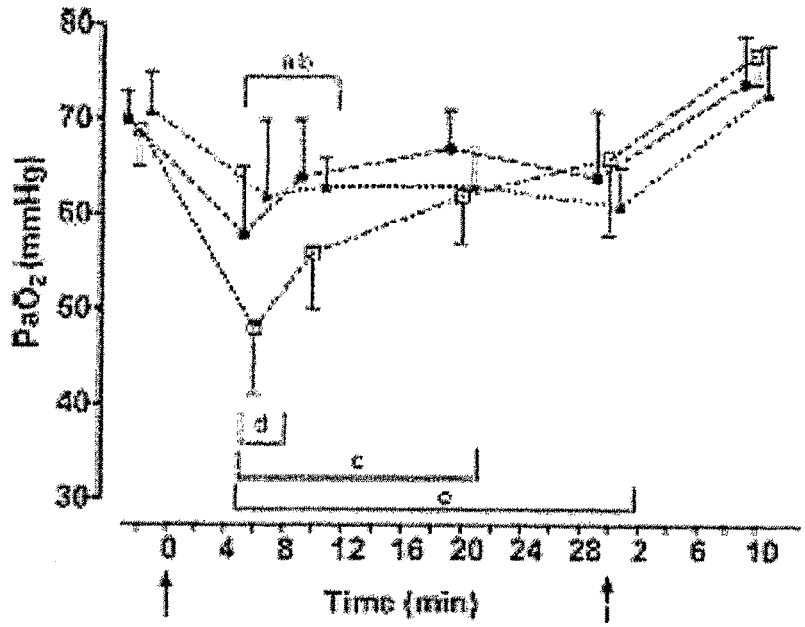

Fig. 3. Drug effects on arterial partial pressure of oxygen ($Pa_{O2}$). Values are $Pa_{O2}$ (means, SD, $n = 8$) of goats injected (solid arrow, time = 0 min) with (intramuscular + intravenous) etorphine + water (□), etorphine + zacopride (●), and etorphine + 8-OH-DPAT (▲). Dashed arrow (time = 30 min) indicates intravenous injection of diprenorphine. $^aP$ <0.05, etorphine + zacopride vs. etorphine + water; $^bP$ <0.05, etorphine + 8-OH-DPAT vs. etorphine + water; $^cP$ <0.05, etorphine + water preinjection vs. postinjection; $^dP$ <0.05, etorphine + zacopride preinjection vs. postinjection; and $^eP$ < 0.05, etorphine + 8-OH-DPAT preinjection vs. postinjection (2-way ANOVA with post hoc SNK test). $Pa_{O2}$ values were not significantly different among the trials before the agents were injected [$F_{(10,70)} = 5.67$, $P$ >0.05].

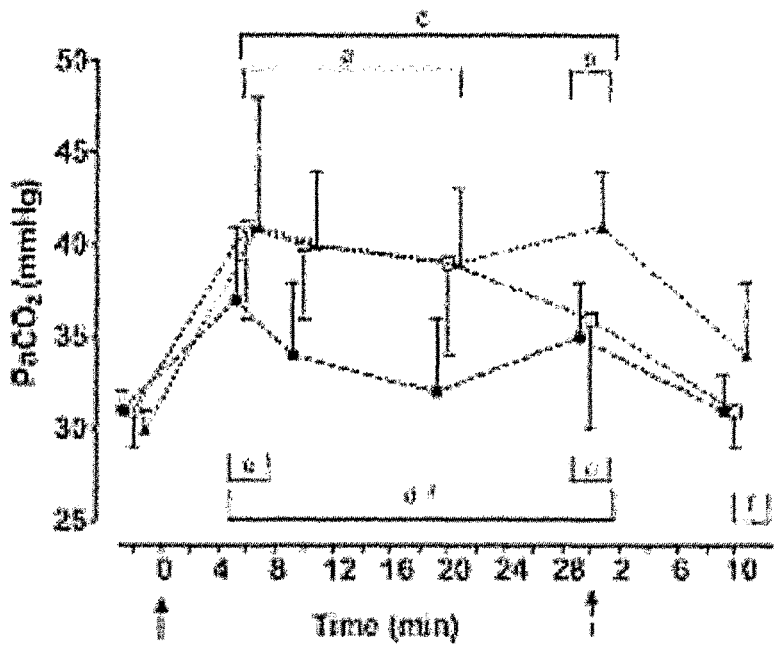

Fig. 4. Drug effects on arterial partial pressure of carbon dioxide ($Pa_{CO_2}$). Values are $Pa_{CO2}$ (means, SD, $n = 8$) of goats injected (solid arrow, time = 0 min) with (intramuscular + intravenous) etorphine + water (□), etorphine + zacopride (●), and etorphine + 8-OH-DPAT (▲). Dashed arrow (time = 30 min) indicates intravenous injection of diprenorphine. $^aP$ <0.05, etorphine + zacopride vs. etorphine + water; $^bP$ <0.05, etorphine + 8-OH-DPAT vs. etorphine + water; $^cP$ <0.05, etorphine + zacopride vs. etorphine + 8-OH-DPAT; $^dP$ <0.05, etorphine + water preinjection vs. postinjection; $eP$ <0.05, etorphine + zacopride preinjection vs. postinjection; and $^fP$ <0.05, etorphine + 8-OH-DPAT preinjection vs. postinjection/reversal (2-way ANOVA with post hoc SNK test). $Pa_{CO2}$ values were not significantly different among the trials before the agents were injected [$F_{(10,70)} = 3.87$, $P > 0.05$].

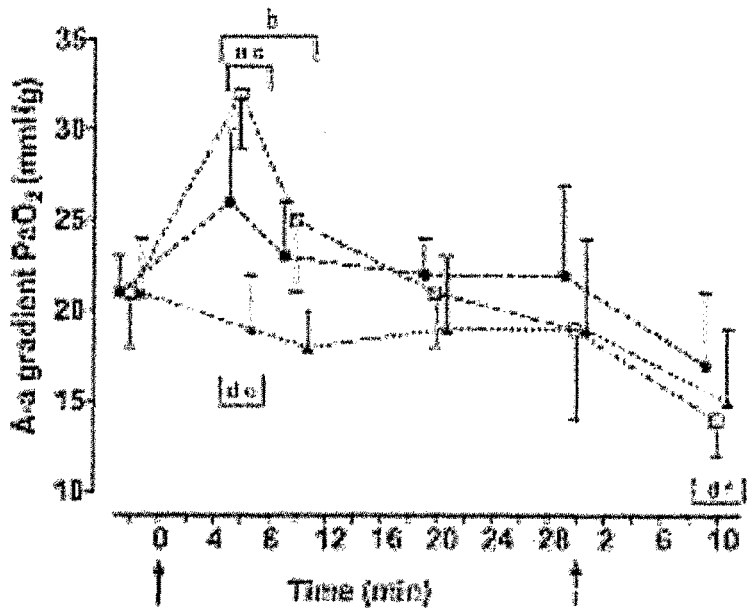

Fig. 5. Drug effects on alveolar-arterial oxygen partial pressure gradient (A-a gradient). Values are A-a gradient (means, SD, $n$ = 8) of goats injected (solid arrow, time = 0 min) with (intramuscular + intravenous) etorphine + water (□), etorphine + zacopride (●), and etorphine + 8-OH-DPAT (▲). Dashed arrow (time + 30 min) indicates intravenous injection of diprenorphine. $^aP$ < 0.05, etorphine + zacopride vs. etorphine + water; $^bP$ <0.05, etorphine + 8-OH-DPAT vs. etorphine + water; $^cP$ <0.05, etorphine + zacopride vs. etorphine + 8-OH-DPAT; $^dP$ < 0.05, etorphine + water preinjection vs. postinjection/reversal; $^eP$ <0.05, etorphine + zacopride preinjection vs. postinjection; and $^fP$ <0.05, etorphine + 8-OH-DPAT preinjection vs. postreversal (2-way ANOVA with post hoc SNK test). A-a gradients were not significantly different among the trials before the agents were injected [$F_{(10,70)}$ = 8.23, $P$ >0.05].

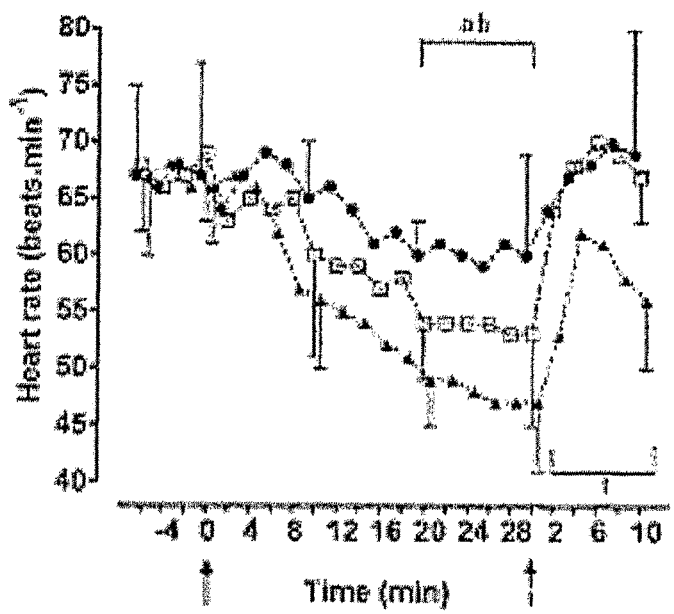

Fig. 6. Drug effects on heart rate. Values are heart rate (means, SD, $n = 8$) of goats injected (solid arrow, time = 0 min) with (intramuscular + intravenous) etorphine + water (□), etorphine + zacopride (●), and etorphine +_ 8-OHDPAT (▲). Dashed arrow (time = 30 min) indicates intravenous injection of diprenorphine. [a]$P < 0.0125$, etorphine + zacopride vs. etorphine + water; and [b]$P < 0.0125$, etorphine + 8-OH-DPAT vs. etorphine + water (1-way ANOVA with post hoc SNK test on areas between the curves). [f]$P < 0.025$, etorphine + 8-OH-DPAT preinjection vs. postreversal (Student's paired $t$-test). Heart rates were not significantly different among the trials before the agents were injected ($F = 0.03$, $P = 0.7$).

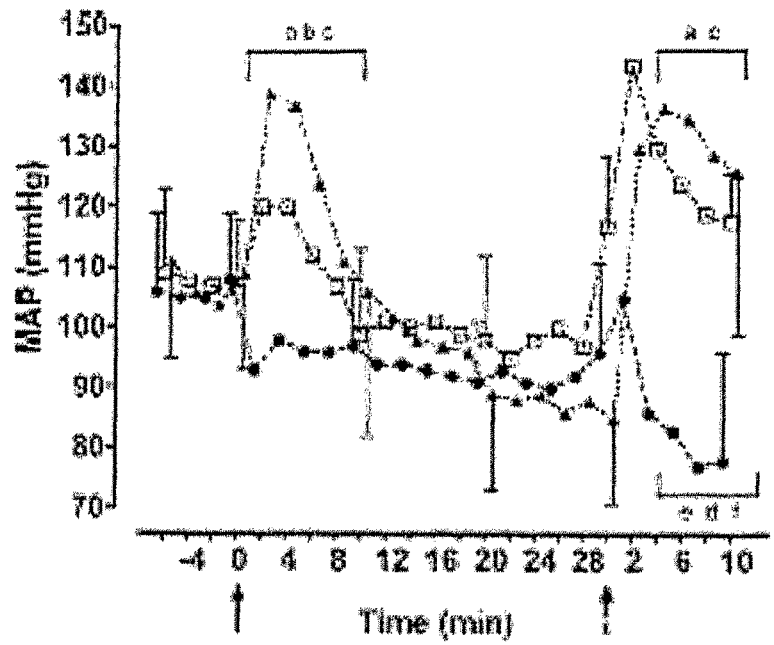

Fig. 7. Drug effects on mean arterial pressure. Values are mean arterial pressure (means, SD, $n = 8$) of goats injected (solid arrow, time = 0 min) with (intramuscular + intravenous) etorphine + water (□), etorphine + zacopride (●), and etorphine + 8-OH-DPAT (▲). Dashed arrow (time = 30 min) indicates intravenous injection of diprenorphine. [a]$P < 0.0125$, etorphine + zacopride vs. etorphine + water; [b]$P < 0.0125$, etorphine + 8-OH-DPAT vs. etorphine + water; and [c]$P < 0.0125$, zacopride + etorphine vs. 8-OHDPAT + etorphine (1-way ANOVA with post hoc SNK test on areas between the curves). [d]$P < 0.025$, etorphine + water preinjection vs. postreversal; [e]$P < 0.025$, etorphine + zacopride preinjection vs. postreversal; and [f]$P < 0.025$, etorphine + 8-OH-DPAT preinjection vs. postreversal (Student's paired $t$test). Mean arterial pressure values were not significantly different among the trials before the agents were injected ($F = 0.41$, $P = 0.67$).

PHARMACEUTICAL COMPOSITION

CROSS-REFERENCE TO PRIOR APPLICATION

This application is the U.S. National Phase of PCT/IB2006/002521, filed Sep. 14, 2006, which claims priority to South African Patent Application Serial No. 2005/07377, filed Sep. 14, 2005 and South African Patent Application Serial No. 2005/09323, filed Nov. 9, 2005. The disclosures of each of these applications is incorporated herein by reference in their entirety. The International Application was published in English on Mar. 22, 2007 as WO 2007/031846 A2 under PCT Article 21(2).

FIELD OF THE INVENTION

This invention relates to a pharmaceutical composition for mammals and, more particularly, to a pharmaceutical composition which enhances the action of an anaesthetic used in both human and veterinary applications.

BACKGROUND TO THE INVENTION

Anaesthetics are important in the treatment of animals for two main reasons. Firstly an anaesthetic, when administered correctly and in the correct dosage, results in a general loss of sensation in an animal which reduces the chances of the animal going into a state of shock when certain medical procedures are performed on it. Secondly, the trance-like state induced by an anaesthetic tends to calm the animal, particularly in veterinary applications and, more particularly where the animal is not domesticated, which also lessens the chances of it going into a state of shock.

Opioids are one of the main classes of drugs which are used in both human and in veterinary medicine to induce anaesthesia, which they do by acting on localised areas of the central nervous system. In the rat it is generally accepted that these areas are the nucleus raphe pontis and the nucleus accumbens both of which contain serotonergic receptors. It is also known that serotonin enhances opioid-induced catatonic or cataleptic immobilisation.

Opioids, unfortunately, also have a number of side-effects. Potentially the most lethal of these side-effects is respiratory depression and the resultant tissue hypoxia which results from the action of opioids on μ-opioid receptors on respiratory neurons in the pre-Bötzinger complex, a collection or network of neurons in the brainstem that generate respiratory rhythm. This complex depends on neurotransmitters, including serotonin, for the modulation of respiratory rhythm.

Studies have demonstrated that serotonergic ligands that bind to the serotonin receptors on respiratory neurons can reverse opioid induced inactivation of respiratory neural networks, the applicant knows of no studies that have shown that serotonergic ligands that bind to serotonergic receptors on respiratory neurons can be used to improve respiratory function and reverse tissue hypoxia that occurs with opioid induced anaesthesia.

The term anaesthesia when used in this specification includes within its scope the inducing of catatonic or cataleptic immobilisation in a human or a non-human mammal for purposes of conducting surgery or reducing sensory perception with a view to reducing shock in emergency situations or to immobilising a non-human mammal to facilitate its capture.

OBJECT OF THE INVENTION

It is an object of this invention to provide a pharmaceutical composition for mammals and, more particularly, to a pharmaceutical composition which enhances the action of an anaesthetic used in both human and veterinary applications, which, at least partly, reduces the risk of respiratory depression and enhances pulmonary and systemic perfusion.

SUMMARY OF THE INVENTION

In accordance with this invention there is provided a pharmaceutical composition characterised in that it contains a serotonergic ligand or any pharmacologically acceptable salt or ester of said serotonergic ligand which acts on a serotonin receptor.

There is also provided for the serotonergic ligand or the pharmaceutically acceptable salt or ester thereof acts on at least one member of the 5-HT family of serotonergic receptors, preferably on one or more of the $5\text{-HT}_{1A}$, $5\text{-HT}_4$ and $5\text{-HT}_7$ serotonergic receptors.

There is further provided for the pharmaceutical composition to be used in conjunction with or include an anaesthetic, preferably an opioid anaesthetic, to be used to induce a state of anaesthesia in humans, alternatively in non-human mammals in which case the anaesthetic can be used to immobilise non-domestic non-human mammals.

The invention also provides for the use of an anaesthetic, preferably an opioid, in the manufacture of a pharmaceutical composition characterised in that the pharmaceutical composition further contains a serotonergic ligand or any pharmacologically acceptable salt or ester of said serotonergic ligand which acts on a serotonin receptor.

There is also provided for the serotonergic ligand or the pharmaceutically acceptable salt or ester thereof acts on at least one member of the 5-HT family of serotonergic receptors, preferably on one or more of the $5\text{-HT}_{1A}$, $5\text{-HT}_4$ and $5\text{-HT}_7$ serotonergic receptors.

There is further provided for the pharmaceutical composition to be used in conjunction with an anaesthetic, preferably an opioid anaesthetic, to induce a state of anaesthesia in humans, alternatively in non-human mammals in which case the anaesthetic can be used to immobilise non-domestic non-human mammals.

There is also provided for the pharmaceutical composition and anaesthetic to be administered to a mammal by intravenous, and/or intra-arterial, and/or intramuscular and/or subcutaneous injection, preferably via a syringe or dart, orally, preferably via a suspension in water, a tablet or a capsule, or transcutaneously via a transcutaneous patch.

The invention also extends to a method of inducing a state of anaesthesia in a mammal, said method comprising administering an effective concentration of the pharmaceutical composition characterised in that the composition contains an anaesthetic and a serotonergic ligand or any pharmacologically acceptable salt or ester of said serotonergic ligand which acts on a serotonin receptor to said mammal.

There is also provided for the serotonergic ligand or the pharmaceutically acceptable salt or ester thereof acts on at least one member of the 5-HT family of serotonergic receptors, preferably on one or more of the $5\text{-HT}_{1A}$, $5\text{-HT}_4$ and $5\text{-HT}_7$ serotonergic receptors.

There is further provided for the pharmaceutical composition to be used to induce a state of anaesthesia in humans, alternatively in non-human mammals in which case the anaesthetic can be used to immobilise non-domestic non-human mammals.

There is also provided for the pharmaceutical composition to be administered to the mammal by intravenous, and/or intra-arterial, and/or intramuscular and/or subcutaneous injection, preferably via a syringe or dart, orally, preferably via a suspension in water, a tablet or a capsule, or transcutaneously via a transcutaneous patch.

According to a further aspect of the invention there is provided for a pharmaceutical composition comprising a serotonergic ligand or any pharmacologically acceptable salt or ester of said serotonergic ligand for use in improving systemic vascular circulation in a mammal.

There is also provided for the serotonergic ligand or the pharmaceutically acceptable salt or ester thereof acts on at least one member of the 5-HT family of serotonergic receptors, preferably on one or more of the $5\text{-HT}_{1A}$, $5\text{-HT}_4$ and $5\text{-HT}_7$ serotonergic receptors.

There is further provided for the pharmaceutical composition to improve vascular circulation of the pulmonary system of the mammal.

There is also provided for the use of a pharmaceutical composition comprising a serotonergic ligand or any pharmacologically acceptable salt or ester of said serotonergic ligand in improving systemic vascular circulation in a mammal comprising administering said pharmaceutical composition to said mammal.

There is also provided for the serotonergic ligand or the pharmaceutically acceptable salt or ester thereof acts on at least one member of the 5-HT family of serotonergic receptors, preferably on one or more of the $5\text{-HT}_{1A}$, $5\text{-HT}_4$ and $5\text{-HT}_7$ serotonergic receptors.

There is further provided for the pharmaceutical composition to improve vascular circulation of the pulmonary system of the mammal.

There is also provided for the use of the pharmaceutical composition in a method of treating a condition responsive to improving pulmonary vascular circulation comprising administering said pharmaceutical composition to said mammal.

There is also provided for the condition to be selected from the group consisting of: pulmonary hypertension, right-sided heart failure, pulmonary oedema.

There is further provided for the pharmaceutical composition to be administered per os, alternatively intramuscularly, intravenously, intra-arterially, subcutaneously, further alternatively intraosseusly, still further alternatively intraspinally or intrathecally, intrarectally or intravaginally or trans-cutaneously.

BRIEF DESCRIPTION OF DRAWINGS

FIG. 1 is a graph showing drug effects on respiratory rate over time. Values are respiratory rate (means, SD, n=8) of goats injected (solid arrow, time=0 min) with (intramuscular+intravenous) etorphine+water (□), etorphine+zacopride (■), and etorphine+8-hydroxy-2-(di-n-propylamino)tetralin (8-OH-DPAT) (◊). Dashed arrow (time=30 min) indicates intravenous injection of diprenorphine. [a]P<0.05, etorphine+zacopride vs. etorphine+water; and [b]P<0.05, etorphine+8-OH-DPAT vs. etorphine+water [1-way ANOVA with post hoc Student-Newman-Keuls (SNK) test on areas between the curves]. [c]P<0.025, etorphine+water preinjection vs. postinjection (Student's paired t-test). Respiratory rates were not significantly different among the trials before the agents were injected (F=3.1, P=0.19).

FIG. 2 is a graph showing drug effects on percent hemoglobin saturation of arterial blood by oxygen. Values are percent saturation (means, SD, n=8) of goats injected (solid arrow, time=0 min) with (intramuscular+intravenous) etorphine+water (□), etorphine+zacopride (■), and etorphine+8-OH-DPAT (◊). Dashed arrow (time=30 min) indicates intravenous injection of diprenorphine. [a]P<0.0125, etorphine+zacopride vs. etorphine+water; and [b]P<0.0125, etorphine+8-OH-DPAT vs. etorphine+water (1-way ANOVA with post hoc SNK test on areas between the curves). [c]P<0.025, etorphine+water preinjection vs. postinjection; and [d]P<0.025, etorphine+8-OH-DPAT preinjection vs. postreversal (Student's paired t-test). Saturation values were not significantly different among the trials before the agents were injected (F=0.1, P=0.9).

FIG. 3 is a graph showing drug effects on arterial partial pressure of oxygen ($Pa_{O2}$). Values are $Pa_{O2}$ (means, SD, n=8) of goats injected (solid arrow, time=0 min) with (intramuscular+intravenous) etorphine+water (□), etorphine+zacopride (■), and etorphine+8-OH-DPAT (◊). Dashed arrow (time=30 min) indicates intravenous injection of diprenorphine. [a]P<0.05, etorphine+zacopride vs. etorphine+water; [b]P<0.05, etorphine+8-OH-DPAT vs. etorphine+water; [c]P<0.05, etorphine+water preinjection vs. postinjection; [d]P<0.05, etorphine+zacopride preinjection vs. postinjection; and [e]P<0.05, etorphine+8-OH-DPAT preinjection vs. postinjection (2-way ANOVA with post hoc SNK test). $Pa_{O2}$ values were not significantly different among the trials before the agents were injected [$F_{(10,70)}$=5.67, P>0.05].

FIG. 4 is a graph showing drug effects on arterial partial pressure of carbon dioxide ($Pa_{CO2}$). Values are $Pa_{CO2}$ (means, SD, n=8) of goats injected (solid arrow, time=0 min) with (intramuscular+intravenous) etorphine+water (□), etorphine+zacopride (■), and etorphine+8-OH-DPAT (◊). Dashed arrow (time=30 min) indicates intravenous injection of diprenorphine. [a]P<0.05, etorphine+zacopride vs. etorphine+water; [b]P<0.05, etorphine+8-OH-DPAT vs. etorphine+water; [c]P<0.05, etorphine+zacopride vs. etorphine+8-OH-DPAT; [d]P<0.05, etorphine+water preinjection vs. postinjection; [e]P<0.05, etorphine+zacopride preinjection vs. postinjection; and [f]P<0.05, etorphine+8-OH-DPAT preinjection vs. postinjection/reversal (2-way ANOVA with post hoc SNK test). $Pa_{CO2}$ values were not significantly different among the trials before the agents were injected [$F_{(10,70)}$=3.87, P>0.05].

FIG. 5 is a graph showing drug effects on alveolar-arterial oxygen partial pressure gradient (A-a gradient). Values are A-a gradient (means, SD, n=8) of goats injected (solid arrow, time=0 min) with (intramuscular+intravenous) etorphine+water (□), etorphine+zacopride (■), and etorphine+8-0H-DPAT (◊). Dashed arrow (time+30 min) indicates intravenous injection of diprenorphine. [a]P<0.05, etorphine+zacopride vs. etorphine+water; [b]P<0.05, etorphine+8-OH-DPAT vs. etorphine+water; [c]P<0.05, etorphine+zacopride vs. etorphine+8-OH-DPAT; [d]P<0.05, etorphine+water preinjection vs. postinjection/reversaf; [e]P<0.05, etorphine+zacopride preinjection vs. postinjection; and [f]P<0.05, etorphine+8-OH-DPAT preinjection vs. postreversal (2-way ANOVA with post hoc SNK test). A-a gradients were not significantly different among the trials before the agents were injected [$F_{(10,70)}$=8.23, P>0.05].

FIG. 6 is a graph showing drug effects on heart rate. Values are heart rate (means, SD, n=8) of goats injected (solid arrow, time=0 min) with (intramuscular+intravenous) etorphine+water (□), etorphine+zacopride (■), and etorphine+_8-OH-DPAT (◊). Dashed arrow (time=30 min) indicates intravenous injection of diprenorphine. [a]P<0.0125, etorphine+zacopride vs. etorphine+water; and [b]P<0.0125, etorphine+8-OH-DPAT vs. etorphine+water (1-way ANOVA with post hoc SNK test on areas between the curves). [f]P<0.025, etorphine+8-OH-DPAT preinjection vs. postreversal (Student's paired t-test). Heart rates were not significantly different among the trials before the agents were injected (F=0.03, P=0.7).

FIG. 7 is a graph showing drug effects on mean arterial pressure. Values are mean arterial pressure (means, SD, n=8) of goats injected (solid arrow, time=0 min) with (intramuscular+intravenous) etorphine+water (□), etorphine+zacopride (●), and etorphine+8-OH-DPAT (◇). Dashed arrow (time=30 min) indicates intravenous injection of diprenorphine. $^{a}P<0.0125$, etorphine+zacopride vs. etorphine+water; $^{b}P<0.0125$, etorphine+8-OH-DPAT vs. etorphine+water; and $^{c}P<0.0125$, zacopride+etorphine vs. 8-OH-DPAT+etorphine (1-way ANOVA with post hoc SNK test on areas between the curves). $^{d}P<0.025$, etorphine+water preinjection vs. postreversal; $^{e}P<0.025$, etorphine+zacopride preinjection vs. postreversal; and $^{f}P<0.025$, etorphine+8-OH-DPAT preinjection vs. postreversal (Student's paired t-test). Mean arterial pressure values were not significantly different among the trials before the agents were injected (F=0.41, P=0.67).

There is also provided for the pharmaceutical composition to be administered in a dosage form which is selected from the group consisting of: a suspension, a tablet, a capsule, a transcutaneous patch and a syringe which may be a conventional syringe, pole syringe or a dart.

BRIEF DESCRIPTION OF ONE EMBODIMENT OF THE INVENTION

The above and additional features of the invention will become apparent from the below described study conducted on domesticated goats using the 5-HT$_{1A}$ and 5-HT$_7$ receptor agonist 8-OH-DPAT, and using the 5-HT$_4$ receptor agonist zacopride.

DETAILED DESCRIPTION OF ONE EMBODIMENT OF THE INVENTION

This study was conducted on eight healthy adult female boer goats (Capra hircus), weighing 40 kg (mean, SD 9) using the 5-HT$_{1A}$ and 5-HT$_7$ receptor agonist 8-OH-DPAT, and using the 5-HT$_3$ receptor agonist zacopride. The goats were housed in climatically controlled indoor pens in Johannesburg, at an altitude of 1,753 meters, on a 12:12-h light-dark cycle. They had access to water ad libitum and were fed on hay and sheep concentrate pellets. The procedures were approved by the University of the Witwatersrand's Animal Ethics Screening Committee (clearance 2004/31/5).

After veterinary inspection, anaesthesia was induced with an intramuscular injection of 2.5 mg/kg ketamine (Anaket; Bayer Animal Health, Johannesburg, South Africa) and 0.04 mg/kg medetomidine (Domitor; Novartis, Johannesburg, South Africa). The goats then were intubated, and anaesthesia was maintained with 1-3% halothane (Fluothane; Astra Zeneca Pharmaceuticals, Johannesburg, South Africa) in oxygen. When inhalation anaesthesia was stable, 0.2 mg/kg atipamezole hydrochloride (Antisedan; Novartis) was injected intramuscularly to reverse the effects of the medetomidine. The left lateral aspect of the neck was shaved and prepared aseptically for surgery. The left carotid artery was translocated surgically to a subcutaneous tunnel according to the modified transposition technique described by Orsini and Roby (32), to allow for subsequent repetitive arterial catheterization in conscious animals. After surgery, a pressure bandage was placed over the site for 24 h. The animals were given a month to recover before the experimental trials commenced.

Etorphine hydrochloride (M99; Novartis) was injected intramuscularly at a dose of 0.06 mg/kg. This dose adequately immobilized and sedated the goats for 30 min. Both 8-OH-DPAT hydrobromide (Tocris, Bristol, UK) and 4-amino-N-1-azabicyclo[2.2.2] oct-3-yl-5-chloro-2-methoxybenzamide hydrochloride (Zacopride; Tocris) were used in their racemic form and were injected intravenously at a dose of 0.5 mg/kg. This dose was established in a pilot dose-response study as a midrange dose that increased the respiratory rate in the goats under etorphine immobilization without causing any harmful side effects. Both 8-OH-DPAT (5 mg/ml) and zacopride (10 mg/ml) were dissolved in sterile injectable water (Kyron Laboratories, Johannesburg, South Africa).

The experiment consisted of three trials in which each goat received etorphine+water (control), etorphine+zacopride, and etorphine+8-OH-DPAT, in random order, at weekly intervals. The goats were weighed 2 days before each trial and were starved for 24 h before the trial to reduce the risk of bloating and regurgitation of ingesta. On the day of the trial, the neck (over the translocated artery) and ears were shaved and disinfected. A 22-gauge intravenous catheter (Introcan; B/Braun, Melsungen, Germany) was placed in an auricular vein and connected to a saline drip (Sabax 0.9% NaCl; Adcock Ingram, Johannesburg, South Africa) for subsequent drug injection. Local anaesthetic (2 ml of Lignocaine; Bayer Animal Health) was injected subcutaneously around the translocated carotid artery to desensitize the overlying skin. An intra-arterial catheter (14 G, FA-04014; Arrow, Erding, Germany) was inserted through a shallow skin incision, about 4 mm long, into the carotid artery. A three-way stopcock valve (Sabex, Johannesburg, South Africa) was attached to the catheter and secured to the neck with adhesive tape (Leukoplast, Hamburg, Germany).

Once the catheters were in place, the goat was moved into a trolley (0.6-1.5 m), where it was restrained by a handler who held the horns. To measure arterial haemoglobin oxygen saturation and heart rate, a veterinary pulse oximeter (Nonin 9847V with 2000T animal transflectance sensor; Nonin Medical, North Plymouth, Minn.) was placed on the skin at the ventral tail base and secured with adhesive tape. Saturation was measured to an accuracy of 3% and heart rates to an accuracy of 2 beats/min. A pressure transducer (1210 ICSensor; MSI Sensors, Fairfield, N.J.) was connected to one arm of the threeway stopcock valve with 1.19-mm tubing (Portex, Kent, UK), and the transducer was attached to a processor constructed for us (School of Electrical Engineering, University of the Witwatersrand) to measure and log mean arterial pressure every 15 s to an accuracy of 2 mmHg. Rectal temperatures were measured with a thermocouple thermometer (BAT-12; Physitemp Instruments, Clifton, N.J.) to an accuracy of 0.2° C. and were used to calculate water vapor pressure in alveolar air. A digital stopwatch was used to record times to recumbency and respiratory rates. Recumbency was determined when a goat could no longer stand in a supine position on its own. The etorphine injection induced immobilization and recumbency.

The level of immobilization was assessed clinically by a veterinarian observing movement, neck tone, and vocalization. The goats were held in sternal recumbency by a handler holding the horns so that the neck was aligned with the spinal column and the head was elevated above the thorax with the nose pointing downward. This positioning allowed for unobstructed eructation of ruminal gas and open upper airways. After 30 min, the action of etorphine was reversed by intravenous injection of 0.096 mg/kg diprenorphine hydrochloride (M5050; Novartis). Data recordings started 6 min. before etorphine injection (injection time=0 min) and continued for 40 min after injection. Heart rate, hemoglobin oxygen saturation, rectal temperature, and respiration rate were recorded every 2 min. Respiration rates were measured by counting breaths, visible by movement of the chest and abdominal wall, over a minute. A 0.5-ml carotid arterial blood sample was drawn 2 min. before etorphine injection, at 6, 10, 20, and 30 min. after etorphine injection, and 10 min. after etorphine reversal. After each sample was drawn, the intra-arterial catheter was flushed with 5 IU/ml heparinized (Heparin; Intramed, Johannesburg, South Africa) saline. Directly after the sample was drawn, a blood gas analyzer (Roche OPTI CCA analyzer+OPTI cassette B; Kat Medical, Johannesburg, South Africa) was used to measure the arterial partial pressure of oxygen ($Pa_{O2}$) and carbon dioxide ($Pa_{CO2}$) in the sample to an accuracy of 1.3 mmHg for PaO2 and 0.4 mmHg for $Pa_{CO2}$.

At the end of each trial, the catheters were removed, and a pressure bandage was placed over the carotid artery for 6 h to prevent haematoma formation in the neck. Once the etorphine trials were completed, the goats were given intravenous injections of 0.5 mg/kg 8-OH-DPAT and 0.5 mg/kg zacopride separately and without etorphine, to assess whether the serotonergic ligands alone had effects on the goats. At the end of the experiment, all of the goats were returned to stock.

All measurements were made indoors, between 0800 and 1300, at an ambient dry bulb temperature between 20 and 22° C. and relative humidity between 21 and 24%. Barometric pressures were measured to an accuracy of 0.1 mmHg by using the on-board barometer of the blood gas analyzer, which we had calibrated against a Fortin mercury barometer (Russel Scientific Instruments, Dereham, UK). Barometric pressure ranged from 628 to 634 mmHg.

A GraphPad Prism version 4.00 for Windows (GraphPad Software, San Diego, Calif.) and Statistica 99 edition (StatSoft, Tulsa, Okla.) for statistical analyses were used to analyse the data collected. All results are reported as means, SD, and P<0.05 was considered statistically significant. The areas between the response curves (over time) to etorphine+water, etorphine+zacopride, and etorphine+8-OH-DPAT were calculated for respiration rate, heart rate, hemoglobin oxygen saturation, and mean arterial pressure for the first 6-min interval (preetorphine+water/ligand administration), for the first, second, and third 10-min intervals and the entire 30 min after etorphine+water/ligand administration, and for the 10 min after diprenorphine administration.

A one-way ANOVA followed by a Student-Newman-Keuls (SNK) post hoc test was used to test for differences between these areas and also for differences in the times to recumbency. A Student's paired t-test was used to determine differences within the trials, between pre- and postetorphine+water/ligand administration, and between preetorphine+water/ligand and postdiprenorphine administration. Bonferroni corrections were applied where necessary.

For $Pa_{O2}$, $Pa_{CO2}$, and alveolar-arterial oxygen partial pressure-gradients (A-a gradients), a two-way ANOVA followed by a SNK post hoc test was used to test for differences between responses to pairs of injections and for differences between pre- and post-etorphine+water/ligand responses and pre-etorphine+water/ligand and post-diprenorphine administration in each trial. The A-a gradients were calculated for an open system (constant pressure) from the formula $FI_{O2}(P_b - P_{H2O}) - Pa_{CO2} - Pa_{O2}$, where $FI_{O2}$ is the fractional inspired oxygen (0.209), $P_b$ is the measured barometric pressure (mmHg), and $P_{H2O}$ is the water vapor pressure of saturated air in the alveoli. $P_{H2O}$ (mmHg) was calculated as $4.58 \exp[(17.27 T_b)/(237.3 - T_b)]$ (3), where $T_b$ is the body temperature taken as per rectum. It was assumed that the partial pressure of carbon dioxide in the alveoli was equal to the $Pa_{CO2}$.

Administration of etorphine caused immobilization and recumbency in all the goats in all three trials. When etorphine was injected with water, it took 93 (SD 13) s (n=8) for the goats to become recumbent. Throughout the 30 min. of immobilization, the etorphine administration caused sedation, muscle relaxation with only slight body movements, and occasional vocalization. When 8-OH-DPAT was injected with etorphine, time to recumbency was reduced significantly (F=1.4, P<0.05) to 51 (SD 21) s, but the subsequent degree of immobilization was not qualitatively different from that following etorphine administration with water. Zacopride administered with the etorphine also significantly (F=1.4, P<0.05) reduced the time to recumbency, to 63 (SD 23) s, but zacopride coadministered did alter the immobilizing effects of etorphine: the goats had increased muscle tone, moved more, and vocalized more than when they received etorphine+water. Although the sedative effects of etorphine seemed to have been reduced by zacopride, the animals were unable to stand or engage in any coordinated movement at any time during the immobilization period. Neither zacopride nor 8-OH DPAT immobilized or sedated the goats when the agents were injected at the same dose but without etorphine. When the ligands were injected without etorphine, the goats became restless, and we were unable to assess any cardiorespiratory variables accurately.

Etorphine administration caused a significant (Student's paired t-test, P=0.013) decrease in respiratory rate: before etorphine+water were injected, the respiratory rate was 27 (SD 9) breaths/min (n+8), and after etorphine+water injection, the respiratory rate decreased to 14 (SD 4) breaths/min, averaged over the 30-min immobilization period (FIG. 1). The respiratory rate returned to preinjection rates once the etorphine action was reversed with diprenorphine (Student's paired t-test, P=0.1). Zacopride (Student's paired t-test, P=0.91) and 8-OH-DPAT (Student's paired t-test, P=0.4), coadministered separately with etorphine, both abolished the decrease in the respiratory rate caused by the etorphine administration. Both drugs significantly (F=5.65, P<0.05) increased the respiratory rate over the full 30-min period of immobilization compared with the etorphine+water trial.

Etorphine administration resulted in a significant (Student's paired t-test, P<0.0001) decrease in the saturation of arterial hemoglobin with oxygen over the 30 min of immobilization (FIG. 2). The decrease in saturation was greatest in the first 10 min of the immobilization. Saturation before etorphine administration was 96 (SD 3)% (n=8) and dropped to as low as 75 (SD 7)% (n=8) after 4 min, with a gradual increase thereafter over time. After diprenorphine injection, saturation returned to near preinjection values (Student's paired t-test, P=0.5). Although saturations significantly decreased after the administration of and etorphine+8-OH-DPAT (Student's paired t-test, P=0.0002), both zacopride and 8-OH-DPAT attenuated the etorphine-induced decrease in saturation. Over the entire immobilization period, saturation in the goats that received etorphine+zacopride was significantly (F=7.18, P<0.05) higher than that when they received etorphine+water. Saturation in the goats that received etorphine+8-OH-DPAT was significantly (F=10.76, P=0.0015) higher than that when they received etorphine+water only over the first 10-min interval after administration. Zacopride (Student's paired t-test, P=0.75) did not alter the return of saturation to preinjection levels after diprenorphine administration, whereas saturation of the goats that received 8-OH-DPAT+etorphine remained moderately depressed (Student's paired t-test, P=0.02).

FIG. 3 shows the effect of administration of etorphine, with and without the serotonergic ligands, on $Pa_{O2}$. $Pa_{O2}$ was 69 (SD 4) mmHg (n=8) before etorphine administration. After the injection of etorphine+water, $Pa_{O2}$ dropped to below 50 mmHg after 6 min. The drop following etorphine+water was significant [$F_{(10,70)}$=5.67, P<0.05] over the first 20 min of immobilization.

Thereafter, $Pa_{O2}$ gradually increased, and returned to preinjection values [$F_{(10,70)}$=5.66, P=0.5] after diprenorphine injection. Zacopride and 8-OH-DPAT attenuated, but did not fully abolish, the etorphine-induced decrease in $Pa_{O2}$, and even though the $Pa_{O2}$ values decreased when zacopride and 8-OH-DPAT were injected with etorphine, both drugs maintained significantly [$F_{(10,70)}$=5.67, P<0.05] higher levels of $Pa_{O2}$ in the goats in the first 10 min of immobilization. Neither zacopride [$F_{(10,70)}$=5.67, P=0.64] nor 8-OH-DPAT [$F_{(10,70)}$=5.67, P=0.95] affected the return of $Pa_{O2}$ values to preinjection values after diprenorphine administration.

Administration of etorphine resulted in a significant [$F_{(10,70)}$=3.87, P<0.05] increase in $Pa_{CO2}$ throughout the immobilization period (FIG. 4). $Pa_{CO2}$ was 31 (SD 2) mmHg (n=8) before etorphine administration. The highest $Pa_{CO2}$ value (41 (SD 5) mmHg) occurred 6 min after the etorphine+water injection and gradually decreased over time, returning to preinjection values after diprenorphine injection [$F_{(10,70)}$=3.87, P=0.94]. Coadministration of 8-OH-DPAT with etorphine had no beneficial effect, and the $Pa_{CO2}$ levels remained significantly [$F_{(10,70)}$=3.87, P<0.001] elevated throughout the immobilization.

Zacopride coadministration significantly attenuated the rise in $Pa_{CO2}$ caused by etorphine. The $Pa_{CO2}$ value for etorphine+zacopride was significantly [$F_{(10,70)}$=3.87, P<0.05] lower than those for etorphine+water and etorphine+8-OH-DPAT in the first 20 min of the immobilization period.

Zacopride [$F_{(10,70)}$=3.87, P=0.93] did not alter the return of $Pa_{CO2}$ values to preinjection values after diprenorphine administration, whereas in the etorphine+8-OH-DPAT trial, $Pa_{CO2}$ values did not return to preinjection values and remained moderately elevated [$F_{(10,70)}$=3.87, P<0.05].

FIG. 5 shows the effect of etorphine administration, with and without coadministration of the serotonergic ligands, on a derived variable, namely, the A-a gradient in the partial pressures of oxygen. The gradient was 21 (SD 3) mmHg (n=8) before administration of etorphine. When etorphine+water were injected, there was a significant [$F_{(10,70)}$=8.23, P<0.0001] increase in the A-a gradient, which resolved progressively during the time course of the immobilization. Coadministration of 8-OH-DPAT with etorphine abolished the increase in the gradient [$F_{(10,70)}$=8.23, P=0.5], and indeed, the gradient remained below the preinjection gradient throughout immobilization. Coadministration of zacopride attenuated [$F_{(10,70)}$=8.23, P=0.003] but did not abolish the effects of etorphine on the A-a gradient [$F_{(10,70)}$=8.23, P<0.002].

After administration of diprenorphine, the A-a gradients dropped significantly below preinjection values in the etorphine_water [$F_{(10,70)}$=8.23, P=0.0004] and the 8-OHDPAT+etorphine [$F_{(10,70)}$=8.23, P=0.005] trials.

FIG. 6 shows the effects of administering etorphine, with and without serotonergic ligands, on heart rate. Heart rate was 67 (SD 5) beats/min (n=8) before etorphine administration. Over the time course of the immobilization, heart rate decreased after etorphine administration, whether or not the ligands were coadministered. In contrast to its effect on respiratory variables, etorphine administration did not affect heart rate immediately. Heart rate was unchanged for at least the first 8 min after etorphine administration. Thereafter, the decline in heart rate was attenuated by coadministration of zacopride but accentuated by coadministration of 8-OHDPAT.

After the second 10-min interval, heart rate was significantly [$F_{(2,7)}$=0.33, P<0.001] decreased after 8-OHDPAT coadministration and increased [$F_{(2,7)}$=0.33, P<0.01] after zacopride coadministration, compared with heart rate following coadministration of etorphine with water. In the etorphine+water and etorphine+zacopride trials, heart rates returned to the preinjection rates after diprenorphine administration, whereas heart rate in the etorphine 8-OH-DPAT trial remained significantly (Student's paired t-test, P<0.0001) lower than the preinjection rate.

FIG. 7 shows the effect of administration of etorphine, with and without the serotonergic ligands, on mean arterial pressure. Mean arterial pressure before the administration of etorphine was 108 (SD 12) mmHg (n=8). Etorphine administration had a biphasic effect on the mean arterial pressure. For the first 6 min after etorphine+water administration, mean arterial pressure increased, and then it gradually decreased throughout the immobilization period.

Coadministration of 8-OH-DPAT with etorphine enhanced the biphasic pressure changes. In the first 10-min interval, mean arterial pressure after coadministration of 8-OH-DPAT with etorphine was significantly (F=0.94, P=0.0015) higher than that following etorphine+water and etorphine+zacopride. Zacopride coadministration attenuated the biphasic effects of etorphine administration and significantly (Student's paired t-test, P=0.025) reduced mean arterial pressure throughout the immobilization. After the administration of diprenorphine, mean arterial pressures were significantly higher than preinjection values in the etorphine+water (Student's paired t-test, P=0.0004) and etorphine+8-OH-DPAT (Student's paired t-test, P=0.01) trials. After the administration of diprenorphine, mean arterial pressure was significantly (Student's paired t-test, P=0.007) lower than preinjection pressure in the etorphine+zacopride trial.

From the above it is evident that, at a dose at which it immobilized goats, the opioid etorphine caused marked respiratory depression. Symptomatically, this depression was evident as a decrease in respiratory rate to about one-half the rate before etorphine administration. The respiratory rate remained low throughout the immobilization period, but, alone, it did not reveal the respiratory status of the animals. Directly after the administration of etorphine and up until 10 min after injection, respiratory depression was the most severe; the animals became clinically hypoxic, taken as $Pa_{O2}$<60 mmHg and percent arterial haemoglobin saturation <85%. Hypoxia resulted from both a decrease in the ventilation, indicated by an increase in $Pa_{CO2}$, and a decrease in diffusion, presumably via a ventilation-perfusion mismatch, indicated by an increase in the A-a gradient in oxygen partial pressure. After 10 min, there was a gradual increase in both the $Pa_{O2}$ and the percent oxygen haemoglobin saturation values, which was brought about predominantly by an improvement in diffusion (compare FIGS. 4 and 5).

That opioids depress respiration is well known. What we have shown, we believe for the first time, is that the depressed respiratory function can be reversed substantially by administration of serotonergic ligands. Coadministration of zacopride or 8-OH-DPAT with etorphine improved the respiratory function of the goats such that PaO2 and arterial haemoglobin saturation remained above levels defining clinical hypoxia. The ligands, which act at different 5-HT receptors, reversed respiratory depression via different physiological mechanisms. Zacopride attenuated the decrease in the respiratory rate and decreased the hypercapnia, indicating improved ventilation. 8-OH-DPAT also attenuated the decrease in the respiratory rate but did not improve ventilation, because PaCO2 remained elevated (FIG. 4).

The main beneficial effect of 8-OH-DPAT was on the pulmonary circulation; it improved diffusion, as indicated by the restoration of normal differences between alveolar and arterial partial pressures of oxygen (FIG. 5), presumably by improving ventilation-perfusion ratios. Zacopride also partially restored the A-a gradient, but its effect was not as great as that of 8-OH-DPAT. In addition to the deleterious effects on the respiratory system, the opioid also affected the cardiovascular status of the goats by inducing bradycardia and transient hypertension (FIGS. 6 and 7). The serotonergic ligands influenced those cardiovascular effects, too. Zacopride abolished the hypertension, whereas 8-OH-DPAT transiently exacerbated the etorphine-induced biphasic changes in mean arterial pressure (FIG. 7). Similarly, zacopride reduced, and 8-OHDPAT enhanced, the bradycardia (FIG. 6).

Both serotonergic ligands improved respiratory function and affected the cardiovascular status without reversing catatonic immobilization, a necessity given that the primary use of etorphine is chemical immobilization of animals. Indeed, coadministration of both zacopride and 8-OH-DPAT with etorphine significantly decreased the time it took for the goats to become recumbent. Thus we have shown that the serotonergic ligands zacopride and 8-OH-DPAT, acting through physiologically distinct mechanisms, improved the respiratory status of goats immobilized with the opioid etorphine, without reversing catatonic immobilization, and zacopride also improved the cardiovascular status of the goats.

It should be noted that the laboratory in which we conducted our experiments was situated at an altitude at which the respiratory status of even intact animals is somewhat different from that at sea level; $Pa_{O2}$, for example, was 70±4 mmHg in the goats before immobilization. However, we have no reason to suspect that the effects of the agents on the respiratory system would differ at altitudes lower than ours, although actual values of variables like the partial pressure of blood gases and the oxygen haemoglobin saturation would differ.

Another potential limitation of our study is that zacopride and 8-OH-DPAT are ligands that act on more than one serotonin receptor. Where we have drawn conclusions about the effects of zacopride or 8-OH-DPAT on one specific receptor, we have based these conclusions on the results from previous studies that have investigated the function of specific 5-HT receptor ligands.

Serotonergic receptors in neuronal pathways play important roles in the modulation of respiratory rhythm. Many studies have examined the effects of serotonin and its congeners on the function of respiratory neurons, specifically during sedative-induced compromise of those neurons. Indeed, the actions of the ligands that we employed have been explored in that context. Sahibzada et al. showed that 8-OH-DPAT reversed the morphine-induced suppression of neuronal activity in anesthetized rats, and Lalley et al. used 8-OH-DPAT to reverse pentobarbital- and ketamine-induced suppression of respiratory neurons in cats. Richter et al. claimed that the effect of 8-OH-DPAT on the neurons generating respiratory rhythm results from its agonism of $5-HT_7$ receptors. They proposed that the reversal of morphine-induced neuronal suppression observed by Sahibzada et al. depended on 8-OHDPAT's action on $5-HT_7$ receptors and not, as Sahibzada et al. had believed, on $5-HT_{1A}$ receptors. Even if the action of 8-OH-DPAT is mediated by the 5-HT7 receptors, $5-HT_{1A}$ receptors also are facilitatory in reversing morphine-induced suppression of respiratory neurons, because buspirone, a $5-HT_{1A}$ agonist that has no effect on the $5-HT_7$ receptor (33), also reversed the suppression. 8-OH-DPAT may well improve the activity of the neurons generating respiratory rhythm through its action on both the $5-HT_{1A}$ and $5-HT_7$ receptors. We believe that 8-OH-DPAT increased respiratory frequency in our goats through its action on respiratory neurons, rather than through the enhancement of the hypoxic drive that the goats experienced after etorphine administration. This belief is supported by the finding that 8-OH-DPAT did not increase respiratory frequency or ventilation rate in hypoxic goats.

8-OH-DPAT's activation of $5-HT_7$ receptors provokes c-AMP formation in respiratory neurons, which then stimulates the respiratory rhythm. It is not clear how 8-OHDPAT's concomitant activation of the $5-HT_{1A}$ receptors could improve respiratory rhythm, although Lalley et al. found that, in anesthetized cats, 8-OH-DPAT's action on $5-HT_{1A}$ receptors prevented prolonged discharge of early inspiratory neurons. In another study, Lalley et al. showed that the effect of 8-OH-DPAT on inspiratory neurons is dose dependent. At lower doses (10-50 μg/kg), 8-OH-DPAT increased the frequency of phrenic nerve discharges in anesthetized cats, but higher doses (50 and 90 μg/kg) suppressed phrenic nerve discharges. In a similar and more recent study, phrenic nerve discharges were decreased even when 20 μg/kg 8-OHDPAT was injected intravenously in cats. We used a much higher dose (500 μg/kg) of 8-OH-DPAT in our goats, and we did not observe any effects consistent with depression of respiratory neurons. Sahibzada et al. also found that 8-OH-DPAT had no depressant effects on rat respiratory neurons when injected at a dose of 100 μg/kg.

In contrast to the uncertainties about the action of 8-OHDPAT on respiratory neurons, the action of zacopride on such neurons seems to derive unambiguously from its agonism of $5-HT_4$ receptors, rather than antagonism of $5-HT_3$ receptors. Zacopride has been shown to be an agonist of the $5-HT_{4a}$ receptor isoform, and Manzke et al. discovered that inspiratory neurons in the pre-Bötzinger complex host both $5-HT_{4a}$ and μ-opioid receptors. Stimulation of the μ-opioid receptors would decrease cAMP in inspiratory neurons and consequently decrease inspiratory drive, whereas stimulation of the $5-HT_{4a}$ receptors would increase cAMP and thus increase inspiratory drive.

In contrast to the degree of investigation on the actions of serotonergic ligands on respiratory neurons, as far as we can establish, no one has investigated the actions of serotonergic ligands on the function of the effecter organs in the respiratory system. It is far from obvious how activity on neurons responsible for respiratory rhythms would translate into effects on the clinically important phenomena of hypoxia and hypercapnia induced by opioids, nor, as we think we have discovered, is it guaranteed that improvement of oxygenation results from actions on respiratory neurons. We have demonstrated that, in goats subjected to opioid immobilization, although 8-OHDPAT improved respiratory rate, it did not improve alveolar ventilation; hypercapnia did not decrease when 8-OH-DPAT was coadministered with etorphine. Nevertheless, 8-OH-DPAT coadministered did improve PaO2. We believe that this increase in $Pa_{O2}$ depended on 8-OH-DPAT countering the effects of the opioid on the pulmonary vasculature. Opioids decrease $Pa_{O2}$, both by reducing alveolar ventilation and by disrupting pulmonary blood perfusion. Pulmonary perfusion decreases under the influence of opioids both because hypoxia causes pulmonary vasoconstriction and because opioids directly cause pulmonary vasoconstriction. They do so by inducing the release of histamine in the lungs and by activating the sympathetic nervous system centrally. We believe that 8-OH-DPAT improved blood oxygenation primarily by reducing pulmonary blood shunting, through its serotonergic effects on the pulmonary vasculature.

Serotonin has a strong vasoactive effect on the pulmonary vasculature. In goats, serotonin causes vasoconstriction in the pulmonary arteries and vasodilation in the pulmonary veins. Serotonin-induced pulmonary vasoconstriction appears to be brought about mainly by the activation of 5-$HT_{2A}$ receptors, to which our ligands did not bind, and pulmonary venodilation by the activation of 5-$HT_4$ receptors. Although no one appears to have explored the effects of 5-$HT_7$ receptor activation in the goat's pulmonary vasculature, we believe that 8-OH-DPAT may have improved the pulmonary perfusion that had been compromised by opioid administration, through its action on 5-$HT_7$ receptors. Our belief is supported by the identification of 5-$HT_7$ receptors in the pulmonary vasculature of many other mammalian species and the observation that 5-$HT_7$ receptor activation causes smooth muscle relaxation. There also is evidence that 5-$HT_7$ receptors may be involved in pulmonary vasodilation in rabbits.

Zacopride causes venodilation in the pulmonary vasculature through its action on 5-HT4 receptors. Venodilation would increase pulmonary perfusion, and although any increase in pulmonary perfusion would have contributed to improving oxygenation, in our goats zacopride acted primarily to improve ventilation, in so doing, reducing hypercapnia and improving both PaO2 and hemoglobin oxygen saturation. It seems likely that the activity of zacopride on pre-Bötzinger neurons, compromised by opioid administration, accounted for the restoration of ventilation.

Although there have been several studies showing that serotonergic ligands act on respiratory networks in the central nervous system, we believe that our study is one of the few showing the effects of serotonergics on blood gases and that it is the first study showing that serotonergics reverse opioid-induced respiratory depression and hypoxia without reversing catatonic immobilization, an outcome that mirrors, for the whole animal, the conclusion of Manzke et al. that a serotonergic ligand can excite respiratory neurons without affecting those involved in analgesia. We also have shown that the effect of serotonergics on the pulmonary vasculature plays an important role in influencing respiratory status, in addition to effects mediated by central respiratory networks. In addition to their effects on the pulmonary vasculature, the ligands also affect the general circulation, with zacopride improving the deleterious consequences of the opioid on blood pressure and heart rate and 8-OH-DPAT worsening them, but only mildly and transiently. Opioids are used in veterinary practice and game management to immobilize mammals. They induce a catatonic immobilization by acting on localized areas in the central nervous system. In the rat, at least, the most prominent of these areas are the nucleus raphe pontis and the nucleus accumbens. Both these nuclei contain serotonergic receptors, and serotonin enhances opioid-induced catatonia.

To the best of our knowledge, no one has identified which serotonin receptors are involved in such enhancement. We have shown that both zacopride and 8-OHDPAT enhanced opioid-induced catatonia in that both reduced time to recumbency in our goats when coadministered with etorphine. Subsequently, though, zacopride somewhat reduced, rather than enhanced, the sedative effects of etorphine. This finding may be explained if zacopride, through its 5-$HT_3$ antagonistic effects, reversed the effects of µ-opioid receptors, thereby resulting in a decrease in opioid-induced hypotonic immobility. It would seem that more than one serotonergic receptor mediates the enhancement of opioid-induced immobilization, but because these ligands each act on two 5-HT receptor types, we are unable to draw any conclusions as to which receptors are involved. We do know that neither ligand, at least at the dose we used, brought about immobilization in its own right. We postulate that the key serotonergic receptors involved in combating opioid-induced respiratory depression, at least in goats, are the 5-HT4 and 5-HT7 receptors, but positive identification of the receptors will require further studies with specific ligands. However, until we also know which serotonergic receptor is responsible for improving opioid-induced catatonic immobilization, we should not conclude that a specific receptor ligand would be the most putative therapeutic agent to improve both immobilization and respiratory welfare.

In summary, we have shown that the serotonergic ligands improve blood oxygenation in goats with respiration depressed by opioid administration, by improving both ventilation and oxygen diffusion. Similar studies have been conducted on the impala, *Aepyceros melampus*, and the similarity of the results obtained indicate that one can, in this instance, extrapolate between species.

It is envisaged that the current invention can be used to enhance the effects of an anaesthetic on both human and non-human mammals and, in the case of the latter, for both domestic and wild mammals. In the case of wild mammals it is envisaged that the composition can be used in a knock-down or tranquilizing dart or pole mounted syringe and, because or the reduction in incidence of respiratory depression, a more effective dose of an opioid can be used in the dart or syringe.

In addition, it is envisaged that the circulatory enhancing effects of the composition will render it useful to treat a variety of, primarily respiratory or pulmonary related conditions usually associated with a reduction in circulation or reduced oxygenation of the blood.

The invention claimed is:

1. A method for improving pulmonary circulation in a mammal, comprising:
    administering to said mammal a pharmaceutical composition comprising an opioid anesthetic and a serotonergic ligand or a pharmacologically acceptable salt or ester thereof,
    wherein the opioid anesthetic is administered in an amount which is effective to induce a state of anaesthesia in the mammal or to immobilize the mammal and the ligand is a serotonin receptor agonist and is administered in a dose of 500 µg/kg, which is effective to improve pulmonary circulation in the anesthetized or immobilized mammal.

2. The method of claim 1, wherein the administration of the serotonergic ligand improves the blood oxygenation of the anesthetized or immobilized mammal.

3. The method of claim 1, wherein the administration of the serotonergic ligand improves both ventilation and alveoli to blood oxygen diffusion in the anesthetized or immobilized mammal.

4. The method of claim 1, wherein the administration of the serotonergic ligand enhances the effect of the opioid anesthetic by reducing the time required to anesthetize or immobilize the mammal.

5. The method of claim 1, wherein the mammal is a human.

6. The method of claim 1, wherein the mammal is a non-human animal.

7. The method of claim 6, wherein the animal is a wild animal.

8. The method of claim 6, wherein the animal is a domesticated animal.

* * * * *